United States Patent [19]

van Zelm

[11] Patent Number: 4,613,179
[45] Date of Patent: Sep. 23, 1986

[54] HAND-HELD GRIPPING DEVICE WITH IMPROVED SUPPORT FOR HANDICAPPED PERSONS HAVING LIMITED FINGER FUNCTION OR WRIST STRENGTH

[76] Inventor: Willem D. van Zelm, 1005 Boyce Ave., Towson, Md. 21204

[21] Appl. No.: 701,235

[22] Filed: Feb. 13, 1985

[51] Int. Cl.⁴ ............................................. B25J 1/02
[52] U.S. Cl. .................................... 294/19.1; 294/25
[58] Field of Search ................. 294/19.1, 22, 23, 25, 294/26, 50.8, 50.9, 57, 58, 115; 224/218, 219, 221, 222, 267

[56] References Cited

U.S. PATENT DOCUMENTS

| 513,875 | 1/1894 | Burriss | 294/25 X |
|---|---|---|---|
| 630,946 | 8/1899 | Strout | 294/50.8 |
| 919,731 | 4/1909 | La May | 294/22 |
| 2,660,467 | 11/1953 | Lenth | 294/50.9 |
| 2,757,952 | 8/1956 | Samuelson | 294/26 |
| 3,482,868 | 12/1969 | Witt | 294/50.9 |
| 4,114,938 | 9/1978 | Strader | 294/19.1 |
| 4,231,603 | 11/1980 | van Zelm | 294/19.1 |

Primary Examiner—Johnny D. Cherry
Attorney, Agent, or Firm—Leonard Bloom

[57] ABSTRACT

An improvement to a gripping device for handicapped persons provides a three-point lateral restraint. The structure for accomplishing this restraint includes a thumb support element, a wrist brace element and an arm support element. These respective elements may be quickly mounted on either side of the device, thereby enabling the device to be used by either right-handed or left-handed persons. A lanyard including a noose is also provided to faciliate convenient manipulation of the gripping device by the free hand of the user. A toggle mechanism includes an over-the-center spring for controlling a pair of gripping tongs.

19 Claims, 24 Drawing Figures

HAND-HELD GRIPPING DEVICE WITH IMPROVED SUPPORT FOR HANDICAPPED PERSONS HAVING LIMITED FINGER FUNCTION OR WRIST STRENGTH

FIELD OF THE INVENTION

The present invention relates to hand-held gripping devices for handicapped persons, and more particularly, to a reaching and gripping device for persons have minimal finger function, severe wrist deformities, or substantial impairment of the trunk musculature.

BACKGROUND OF THE INVENTION

The prior art gripping devices, as exemplified by my U.S. Letters Pat. No. 4,374,600 issued on Feb. 22, 1983, generally include a forward arm member having a suitable gripping means, such as gripping tongs, carried forwardly thereon. A rearward arm member is hinged to the forward arm member, such that the forward arm member may be pivoted and swung downwardly relative to the rearward arm member. The rearward arm member is provided with a palm brace depending therefrom; and a control mechanism is carried by the rearward arm member, forwardly of the palm brace, for controlling the opening and closing of the gripping tongs. This device enables a handicapped user to reach a certain object and pick it up with the gripping tongs. This device is especially useful to paraplegics who are confined to wheelchairs, and substantially increases their ability to perform useful functions in the home and on the job.

While useful and adequate for the purposes intended, nevertheless, handicapped users may have a severely limited gripping ability, such that in the installation and manipulation of the gripping device, as well as in its removal from the user, problems are frequently encountered. Additionally, the use of these gripping devices also imposes a variety of stresses on the forearm, wrist and hand of the handicapped user. Because the user's limited functional manipulative capacity may stem from severe arthritis or spinal injury, it is desirable that, first, effective use not require finger function, and second, that the wrist be fully supported and essentially immobilized.

SUMMARY OF THE INVENTION

Accordingly, it is an object of the present invention to provide an improved gripping device including a bracing means having a lateral restraint system for a handicapped user having no finger or wrist function.

It is another object of the present invention to provide a bracing means including a thumb support used in conjunction with the conventional palm brace, and further including a wrist brace and an arm support, to form a three-point lateral restraint system.

It is yet another object to provide a bracing means which is readily removable and is reversible, thereby adapting the device to either right-handed or left-handed handicapped users.

It is a further object to provide a bracing means that is easily installed and removed without the need of finger function on the part of the user, yet provides a secure attachment, and support for those users suffering from wrist disease, deformity or injury.

It is a still further object to provide a bracing means for a gripping device, which is inexpensive to produce, yet is strong, lightweight, reliable and convenient to use.

It is a yet further object to provide an activation lanyard for a gripping device, which can be used to activate the gripping device by a person having limited gripping capacity or finger function.

In accordance with the teachings of the present invention, there is herein disclosed a preferred embodiment thereof, constituting an improved gripping device to aid handicapped persons in reaching and picking up objects. The device includes a forward arm member carrying a gripping means, such as gripping tongs, forwardly thereon. A rearward arm member, having a right side and a left side, is pivotably connected to the forward arm member. A control mechanism, constituting a toggle mechanism, is movably mounted on the rearward arm member for selectively controlling the gripping means. A palm member is secured to the rearward arm member and depends therefrom. A bracing means is provided which includes a wrist brace mounted on the rearward arm member rearwardly of the palm brace. The wrist brace is positioned proximally to the wrist of the user when the palm brace is pressed by the user, thereby limiting the non-functional flexion or extension of the wrist joint. A thumb support is removably mounted on the palm brace and extends laterally therefrom.

In accordance with the further teachings of the present invention, an arm support is mounted on the rearward arm member rearwardly of the wrist brace. The arm support at least partially surrounds the forearm of the user and cooperates with the wrist brace to substantially limit the movement of the wrist joint of the user by providing a multi-point lateral restraint.

In accordance with the still further teachings of the present invention, an actuating lanyard is connected to the control mechanism and may, if desired, include a self-adjusting noose adapted to be worn by the free hand of the user. The control mechanism is thus actuated by applying tension on the lanyard.

Preferably, the thumb support, wrist brace and arm support are each made from vinyl-coated aluminum wire and are bent to form respective U-shaped pieces that may be quickly mounted to either the right or left side of the improved gripping device.

Viewed in another aspect, the present invention provides a gripping device to aid a handicapped person in reaching and picking up an object, the gripping device including a pair of gripping tongs. A resiliently-biased pivotable control, including a toggle mechanism having an over-the-center spring action, is provided for selectively actuating the gripping tongs. A bracing means provides a restraint for the wrist and forearm of the user. The bracing means includes a thumb support and further includes a wrist brace. Means are provided for removably attaching the thumb support and wrist brace to either side of the gripping device, thereby facilitating use by either a right-handed or a left-handed person.

Viewed in yet another aspect, the present invention provides a gripping device to be used by a handicapped person in reaching and picking up objects, wherein the device includes a forward arm member, a pair of gripping tongs carried by the foreward arm member and extending forewardly therefrom, and a rearward arm member. Means including a hinge are provided for connecting the forward and rearward arm members, thereby allowing the forward arm member to be folded back and over the rearward arm member, and a releasable means retains the forward arm member in its folded back position on the rearward arm member. Means are provided for limiting the downward pivotal movement of the forward arm member relative to the rearward arm member, such that the forward and rearward arm members when extended are in substantially a straight line relative to each other. A toggle control mechanism is carried by the rearward arm member and has an over-the-center spring action for selectively opening and closing the gripping tongs. Bracing means provide a three-point lateral restraint, while lining up the gripping device as a straight line extension of the forearm.

These and other objects of the present invention will become apparent from a reading of the following specification taken in conjunction with the enclosed drawings.

DESCRIPTION OF THE PREFERRED EMBODIMENT

Figure 1:
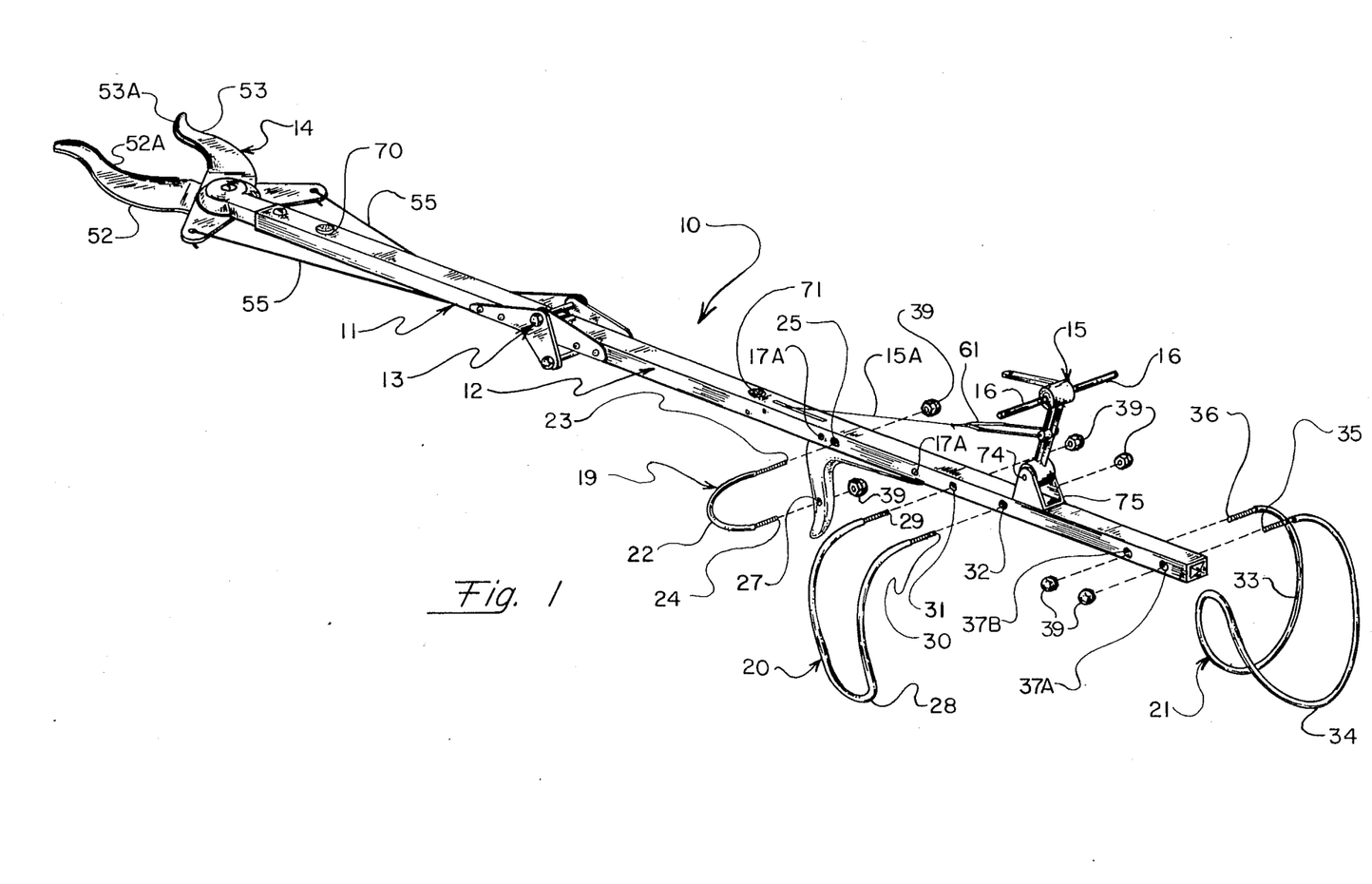
FIG. 1 is a partially exploded perspective of the improved gripping device of the present invention, showing the removable components of the bracing means adapted for a right-handed user, the actuating lanyard being omitted for ease of illustration.
Figure 2:
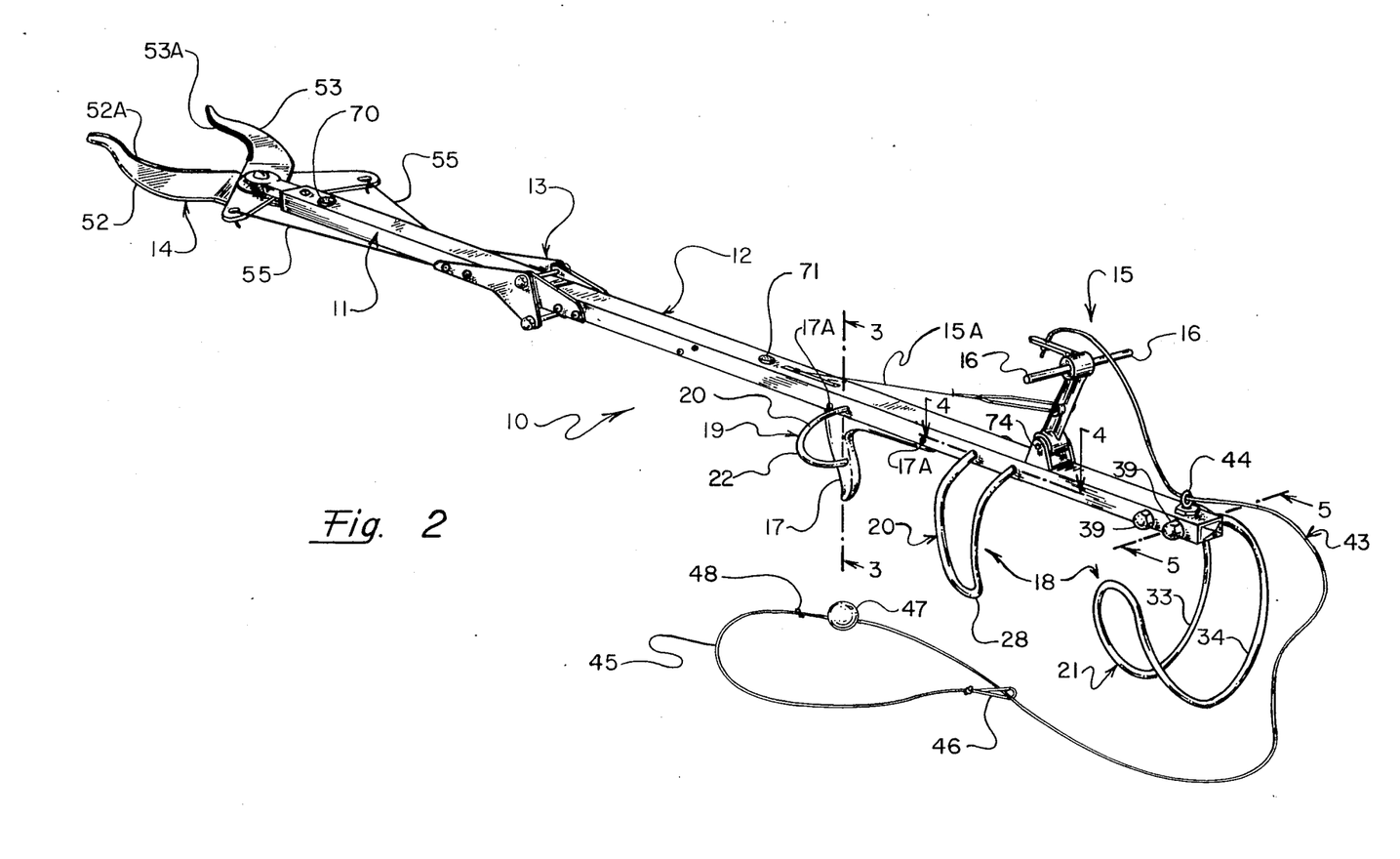
FIG. 2 is a perspective of the improved gripping device of FIG. 1 (in assembled form) showing the improved bracing means, and further showing an activating lanyard including a self-adjusting noose.

With reference to FIGS. 1 and 2, the improved gripping device 10 of the present invention (sometimes referred to as a "reacher") is adapted for convenient use by handicapped persons whose reaching or gripping ability is impaired by spinal injury, arthritis, disease or trauma to the finger, wrist, hand or torso. The gripping device 10 includes a forward arm member 11 pivotably attached to a rearward arm 12 by a suitable hinge 13. The forward arm member carries a gripping means, such as a gripping tongs 14, forwardly thereof. The gripping tongs 14 are activated by a resiliently-biased pivotable control mechanism 15 through a suitable flexible member such as cord 15A (as hereinafter described in detail). The control mechanism constitutes a toggle mechanism having an over-the-center spring and further having laterally-extending prongs 16. These prongs aid in the activation of the gripping tongs by parts of the user's body, such as fingers or the heel of the palm. As hereinafter described, pivotable rotation of the toggle control mechanism away from the gripping tongs brings the tongs together, thereby enabling the device to pick up an object; and pivotable rotation of the toggle control mechanism forwardly thereof separates the gripping tongs, thereby releasing the object. The device further includes a palm brace 17 secured to the rearward arm member by spring pins 17A (FIG. 1) and depending therefrom.

The improved gripping device of the present invention is provided with a bracing means generally denoted at 18. The bracing means provides a multi-point restraint system, which in the preferred embodiment, constitutes a three-point restraint system. The bracing means 18 includes a thumb support element 19, a wrist brace element 20 and an arm support element 21. The thumb support 19 is removably mounted on the palm brace and rearward arm support, respectively; the wrist brace 20 is removably mounted on the rearward arm member rearwardly of the palm brace; and the arm support 21 is removably mounted on the end of the rearwardly arm member, as shown more clearly in FIG. 2.

Figure 3:
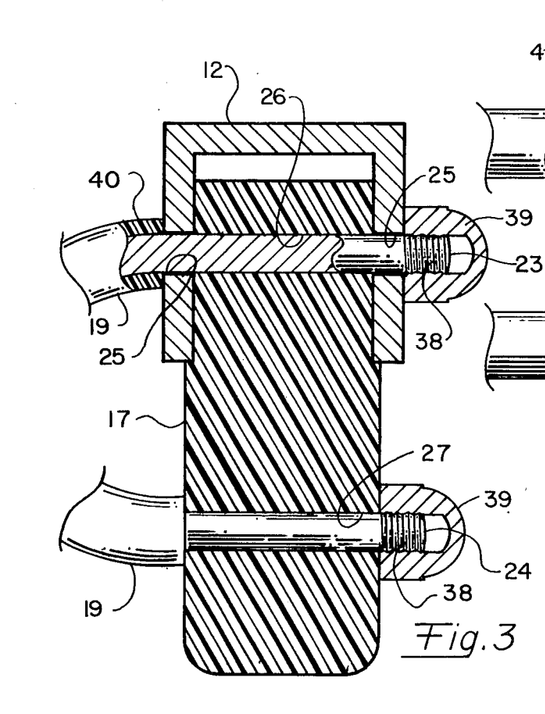
FIG. 3 is a detailed cross-sectional view taken across the lines 3—3 of FIG. 2, drawn to an enlarged scale, and showing the removable reversible mounting of the thumb support on the palm brace and rearward arm members, respectively.

With further reference to FIG. 3, the thumb support element 19 is preferably formed as a substantially U-shaped wire lying in a plane substantially at right angles to the gripping device. The U-shaped wire has a bight 22 and further has a pair of free ends 23 and 24. The rearward arm member has aligned apertures 25 formed therein, which communicate with aperture 26 in the palm grip, for selective receipt of the end 23. The palm brace further has an aperture 27 formed therein for selective receipt of the end 24. In this manner, the U-shaped wire forming the thumb support 19 may be placed on either the left side or the right side of the gripping device. When used on the left side, the gripping device is adaptable for use by right-handed persons; and if used on the right side, the gripping device is adaptable for use by left-handed persons. The respective apertures may be through communicating apertures (as shown) or may be respective closed apertures, if desired.

Figures 4, 4A, 5:
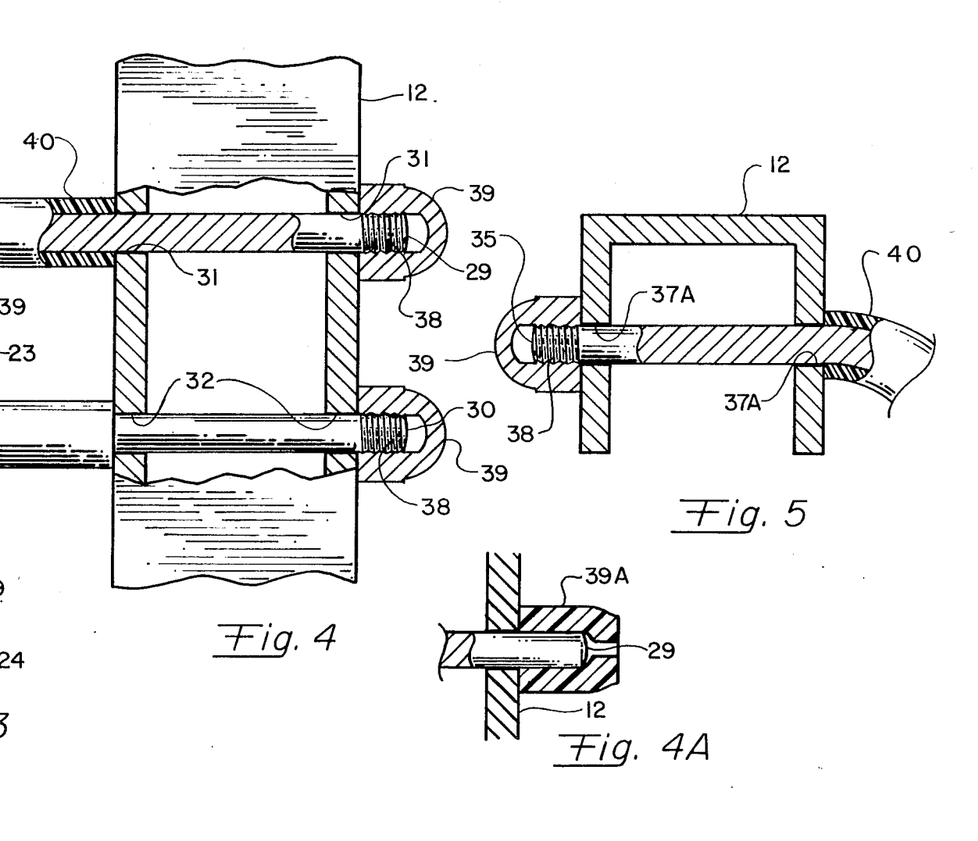
FIG. 4 is a detailed cross-sectional view taken across the lines 4—4 of FIG. 2, drawn to an enlarged scale, and showing the removable reversible mounting of the wrist brace on the rearward arm member.
FIG. 4A corresponds to a portion of FIG. 4, but shows an alternate means for retaining the supporting elements.
FIG. 5 is a detailed cross-sectional view taken across the lines 5—5 of FIG. 2, drawn to an enlarged scale, and showing the removable reversible mounting of the arm support on the rearward arm member.

With further reference to FIG. 4, the wrist brace element 20 is also preferably formed as an elongated substantially U-shaped wire, a portion of which lies in a plane substantially parallel to the longitudinal axis of the gripping device. This U-shaped wire has a bight 28 and further has a pair of ends 29 and 30. The rearward arm member has pairs of spaced apertures 31 and 32. The ends 29, 30 of the U-shaped wire-formed wrist brace 20 may be removably received in the respective aperture 31, 32, thereby facilitating either left-handed or right-handed use of the gripping device. As shown in FIG. 2, the wrist brace is adapted for use by a right-handed person.

With further reference to FIG. 5, the arm support element 21 is also preferably formed as a U-shaped wire having a pair of spaced-apart C-shaped loops 33 and 34 forming a support for the forearm of the user. The U-shaped wire-formed arm support also has a pair of free ends 35 and 36, and the rearward portion of the rearward arm member is provided with complementary pairs of aligned apertures 37A and 37B. With this arrangement, the U-shaped wire-formed arm support partially surrounds the user's forearm and may be removably mounted on either the left or right side of the rearward arm member.

The U-shaped wire-formed supporting elements (19, 20 and 21) may be retained on the gripping device by any suitable means. In a preferred embodiment, as shown in the drawings, the respective ends of each of the wire-formed supporting elements are threaded, as at 38, to receive respective nuts 39.

Thus, it will be appreciated that the thumb support and wrist brace may be mounted on the left side of the gripping device for use by a right-handed person or, in the alternative, on the right side of the gripping device for use by a left-handed person.

Each of the U-shaped wire-formed supporting elements, constituting the thumb support, wrist brace and arm support, respectively, may be made of a readily-available aluminum wire for convenience and economy of manufacture. Each of the wires may be provided with a vinyl coating 40 for user comfort and product attractiveness. The aluminum wire is relatively soft and somewhat flexible and hence may be bent conveniently so as to be tightened or loosened to customize the gripping device of the present invention to the needs of a particular patient. With the aluminum wire, push-on frictional sleeves 39A shown in FIG. 4A, may be employed to facilitate quick and easy replacement of the supporting elements.

Figures 6, 7:
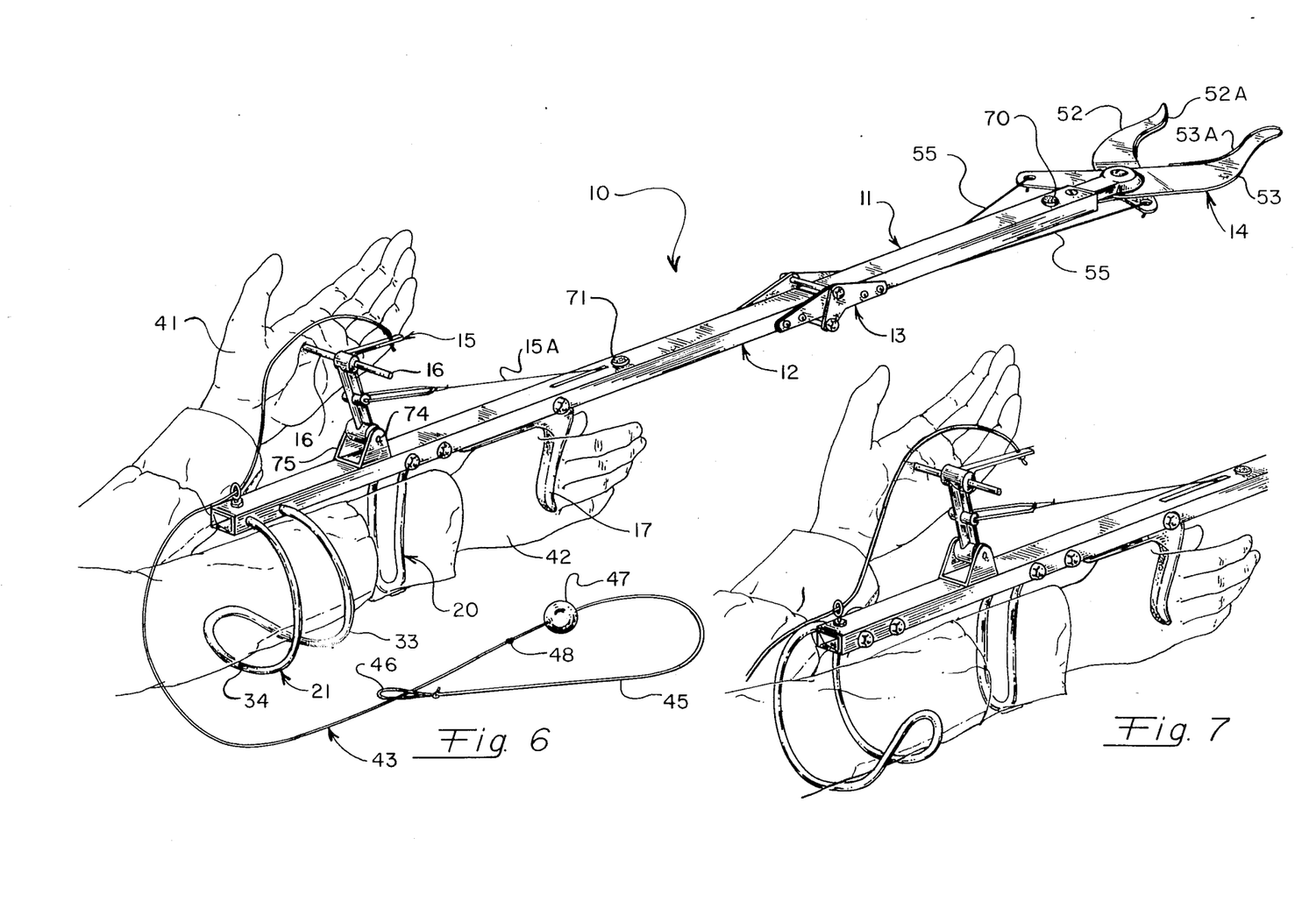
FIG. 6 is a further perspective view, taken from the other side of the gripping device as shown in FIG. 2, and showing a typical usage of the gripping device.
FIG. 7 corresponds to a portion of FIG. 6, but shows the arm support reversed and mounted on the left side of the gripping device.

With further reference to FIGS. 6 and 7, the gripping device 10 of the present invention is shown mounted on the user's right hand 42, and the user's left hand 41 is shown engaging one of the prongs 16 on the control mechanism 15 to close the gripping tongs 14. In FIG. 6, the thumb support 19 (hidden from view) and the wrist brace 20 are mounted on the left side of the gripping device 10, while the arm support 21 is mounted on the right side thereof. However, as shown in FIG. 7, the thumb support 19, wrist brace 20 and arm support 21 are all mounted on the left side. With the arrangement in FIG. 6, the gripping device will provide better support, but is slightly more difficult to get into, than the arrangement in FIG. 7. Either arrangement, however, is equally consonant with the teachings of the present invention.

With the improvement of the present invention, the wrist of the handicapped user is substantially immobilized, that is, substantially restrained against movement. The wrist may be immobilized against extension, flexion or ulnar. Extension constitutes an "out" movement, that is, away from the body. Flexion constitutes an "in" movement, that is, towards the body. Ulner constitutes downward or lower deflection of the wrist. The wrist brace immobilizes the wrist against either extension or flexion. The palm brace provides a lateral restraint. The thumb support (mounted in juxtaposition to the palm brace) holds the wrist up, that is, the thumb support provides a vertical restraint preventing the wrist from dropping downwardly.

When worn on the user's right hand, the palm brace is placed in the notch formed by the thumb and index finger of the user's right hand and across the palm to the extent possible. The right thumb is placed through the thumb support. The wrist brace lies adjacent to the right wrist interior, thereby preventing non-functional wrist extension. In the case of wrist flexion, the support position may be reversed to the wrist exterior. The forearm rests within the arm support, as shown in either FIG. 6 or FIG. 7. In this configuration, the bracing means or restraint system provides a three-point lateral restraint, preventing non-functional flexion or extension of the wrist and further providing straight line extension of the forearm, thereby eliminating unnecessary torsional stress to the arm, wrist or hand.

Thus, the improved gripping device 10 of the present invention completely satisfies the need of persons with minimal or no finger function, severe wrist deformities, and little or minimally functional trunk musculature. The arm support relieves virtually all stress on the radial side of the wrist. The wrist brace is located on the inside of the gripping device to prevent non-functional wrist extension; and in the case of wrist flexion, the wrist brace would be on the outside. The thumb support will prevent the user's wrist and palm from dropping with respect to the gripping device (or "reacher") 10.

The patient's therapist may adjust the respective supports and braces so that when the user's thumb is placed inside the thumb support on the palm brace, it will combine with the wrist brace and arm support to provide a three-point lateral restraint, while lining up the gripping device as a straight line extension of the forearm. As a result, the gripping device is completely stabilized and exerts very limited, if any, torsional stress on the forearm and without the need of any finger function.

With reference again to FIG. 2, the improved gripping device 10 of the present invention may be provided with an activating cord or lanyard 43. One end of the lanyard is attached to the control mechanism. The lanyard passes through an eyelet 44 which serves as a guide for the lanyard cord. A self-adjusting noose 45 is provided. The noose may be worn around the full wrist of the user or about any part of the user's body over which sufficient control may be exercised. The noose is formed by passing the cord through a small loop 46 formed at the end opposite the point of attachment to the toggle of the control mechanism. A small, yet relatively dense ball 47 is slidably carried by the noose. A knot 48 limits the travel of the ball, thereby limiting the noose size to a predetermined minimum. The ball may also be used to enlarge the noose where only one of the user's hands is available. When the cord is held near the loop 46 the ball will slide downward under the influence of gravity, thereby pulling more cord through the loop and enlarging the noose. The length of the cord and the noose are adapted to the specific needs of an individual user.

Figure 8A:
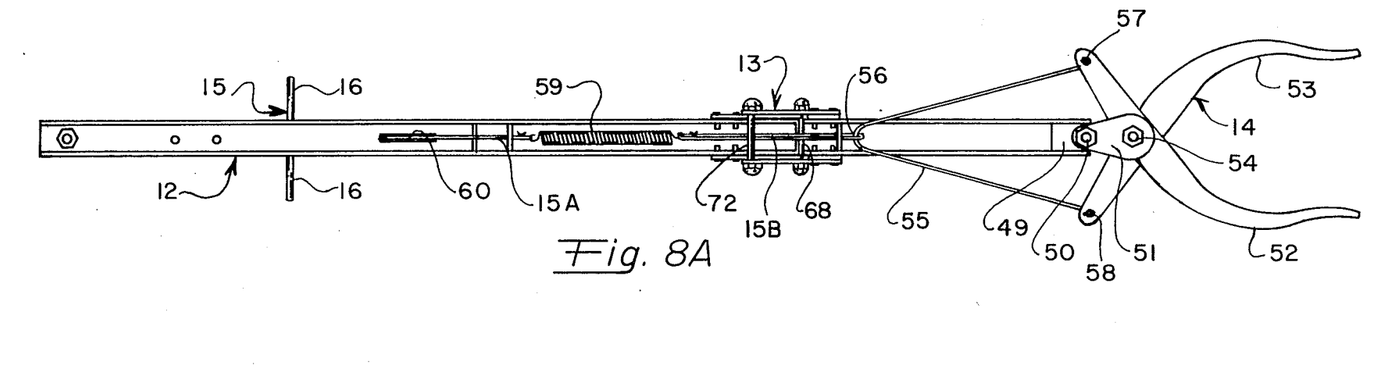
FIG. 8A is a bottom plan view of the gripping device (the palm brace, thumb support, wrist brace and arm support being omitted for ease of illustration) showing the position of the toggle control mechanism when the tongs are open, and further showing the spring between the tongs and the control toggle, the spring preferably being nested within the channel-shaped rearward arm member of the gripping device.
Figure 8B:
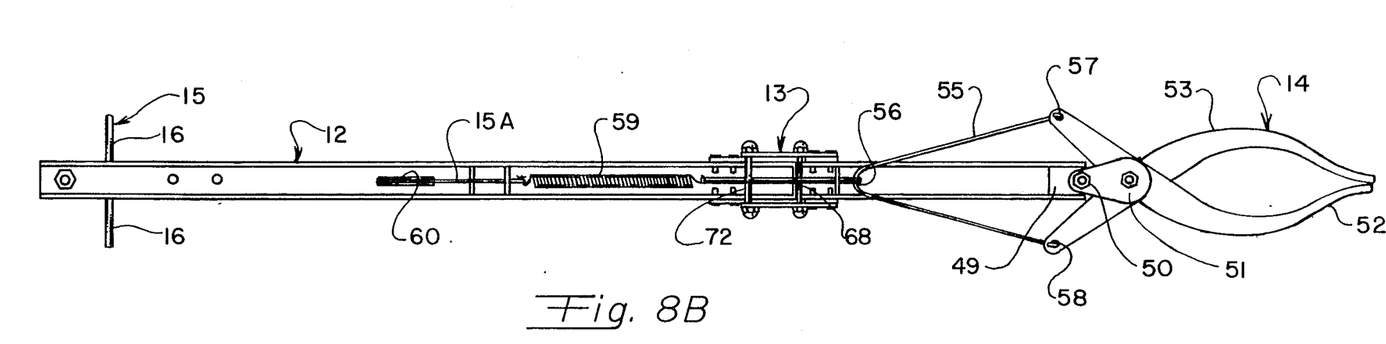
FIG. 8B is a bottom plan view of the gripping device, corresponding substantially to FIG. 8, but showing the position of the toggle control mechanism and the spring when the tongs are closed.

With reference again to FIGS. 1-7, and with further reference to FIGS. 8A and 8B, the forward arm member 11 and rearward arm member 12 preferably are each formed from a U-shaped channel. The forwardmost end of the forward arm member has a support block 49 secured therein by a suitable fastener 50 constituting a bolt and a nut. A plate 51 is mounted on the support block (by the fastener) and extends forwardly therefrom. The gripping tongs 14 include respective gripping tong members 52 and 53 having rubber facings 52A and 53A, respectively. The gripping members are pivotably mounted to each other and to the plate by a suitable fastener 54. A Vee-shaped wire 55 has a bight 56 and a pair of free ends forming hooks 57, 58, respectively, mounted in the rearward portions of the gripping tong members 52, 53, respectively. A cord 15B is tied between the bight of the Vee-shaped wire and one end of a coil spring 59. The other end of the spring 59 is connected to the toggle control mechanism 15 by the cord 15A. The cord 15A extends through a slot 60 in the rearward arm member and is tied to a wire clip 61 carried by the toggle control mechanism.

With reference to the schematic sequence views of FIGS. 9-15, the operation of the gripping device of the present invention will now be described. In general, when the toggle control mechanism 15 is forward, the gripping tong members 52, 53 are open, which is the normal position; and when the toggle control mechanism 15 is rearward, the gripping tong members 52, 53 are closed. More specifically, the toggle control mechanism may be engaged and pivotably swung back, partially from the position shown in FIG. 9 to the position shown in FIG. 11, at which time the gripping tong members 52, 53 begin to approach each other. Rearward movement of the toggle control mechanism is continued (through FIGS. 11 and 12) until the toggle reaches the position of FIG. 13, at which time the "over-the-center" spring toggle action takes over to snap the toggle to the position shown in FIG. 14. At the point, the toggle remains in its fully retracted position, the spring 59 is extended, and the gripping tong members 52, 53 remain closed even though the toggle control mechanism is no longer engaged by the user. The user does not have to continually hold the toggle control mechanism, which is another advantage of the improved gripping device of the present invention. The toggle control mechanism may be engaged in any suitable manner, such as by engagement with the palm of the user's other hand, or by the noose on the lanyard, or by simply gripping the lanyard cord with the teeth.

Figure 9:
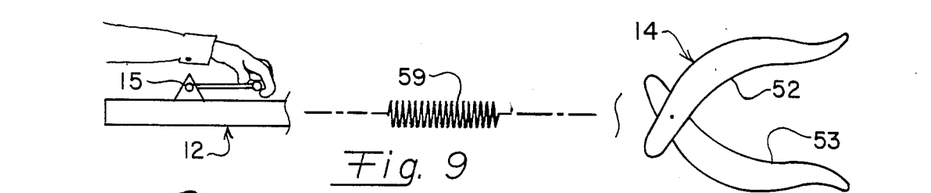
FIGS. 9-15, respectively, are schematic exploded views showing the positions of the toggle control mechanism, the spring, and the gripping tongs, respectively, and sequentially illustrating the over-the-center actuation of the spring-loaded toggle control mechanism for the gripping tongs, (the gripping tongs being displaced ninety degrees relative to the toggle control mechanism for ease of illustration).
Figure 10:
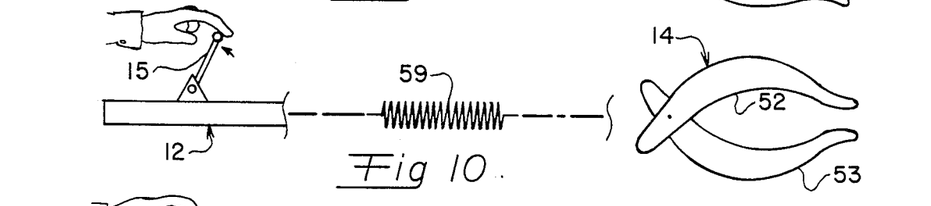
Figure 11:
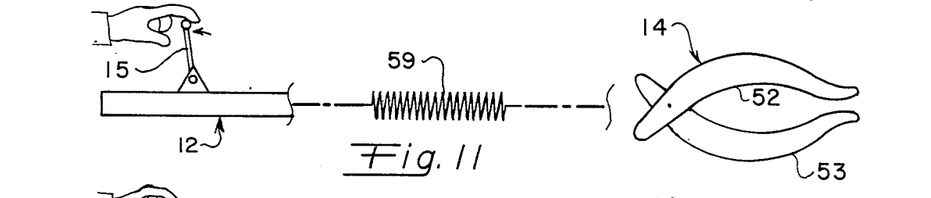
Figure 12:
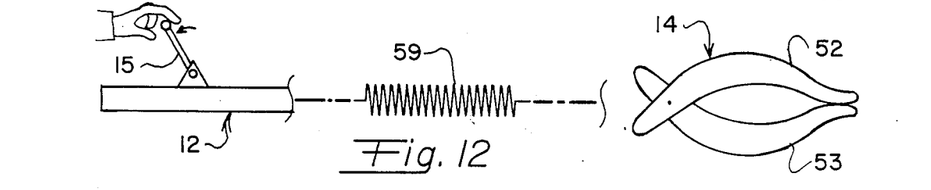
Figure 13:
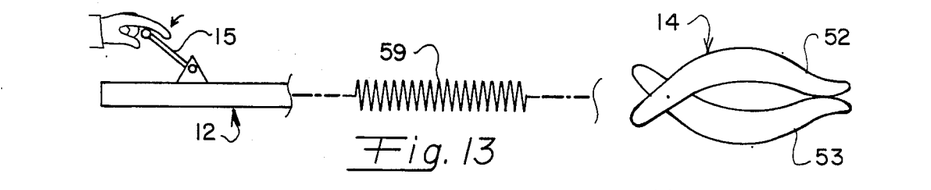
Figure 14:
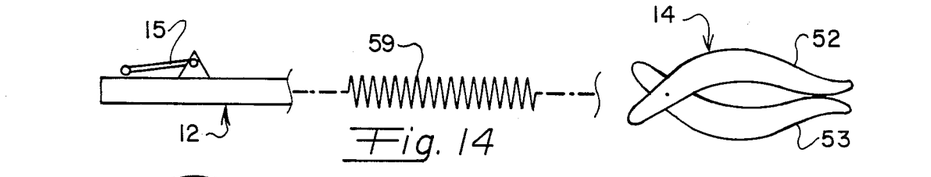
Figure 15:
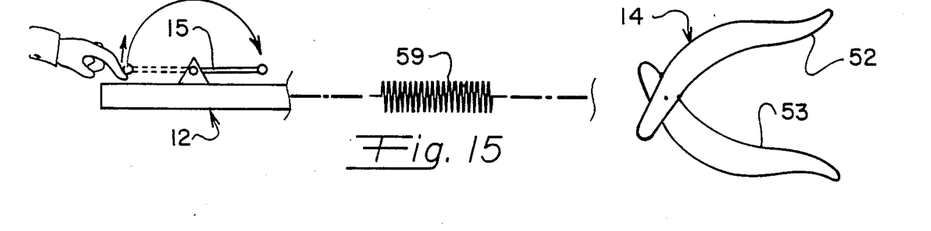

To release the gripping tong members 52, 53, the toggle control mechanism 15 is pivoted upwardly, as shown in FIG. 15; and when the toggle reaches the position corresponding substantially to that of FIG. 13, the spring quickly flips the toggle over and releases the gripping tong members, as shown in FIG. 15, corresponding to the original position of FIG. 9.

The combination of the rearward mounting of the toggle control mechanism above the rearward arm member, its convenient actuation by use of the laterally-extending prongs on the toggle, and its over-the-center spring action for opening and closing the gripping tongs, in combination with the bracing means for the user's wrist and forearm, is another important feature of the present invention.

Figures 16, 17, 18, 19, 20, 21, 22:
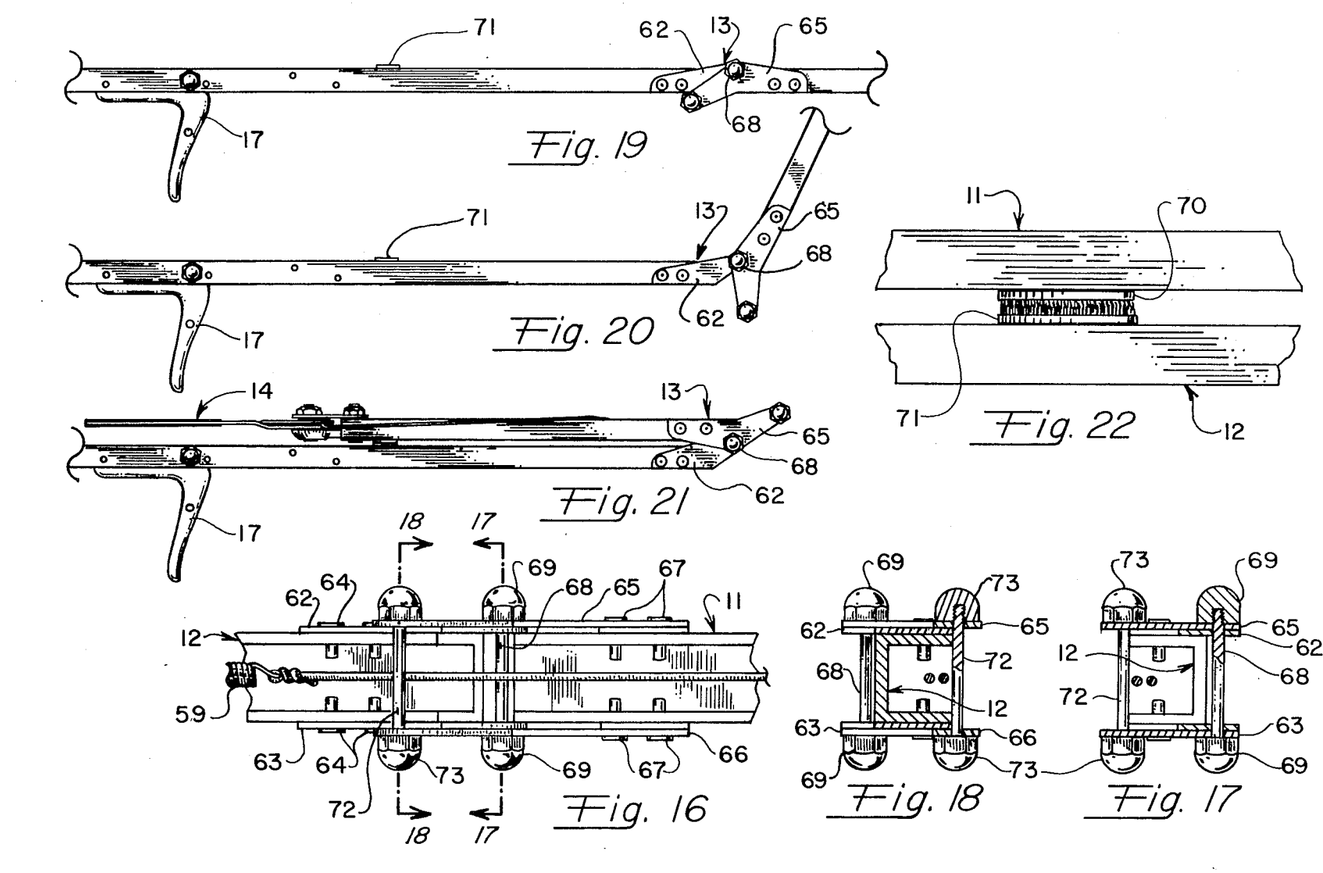
FIG. 16 is a bottom plan view of the hinge between the forward and rearward arm members, and drawn to an enlarged scale.
FIG. 17 is a detail section view thereof, taken across the lines 17—17 of FIG. 16, showing the hinge pin.
FIG. 18 is a detailed section view thereof, taken across the lines of FIG. 16, showing the stop pin.
FIGS. 19-21, respectively, are schematic side elevational views of the forward and rearward arm members, and sequentially illustrating the manner in which the forward arm member is folded back over a portion of the rearward arm member.
FIG. 22 is an enlarged portion of FIG. 21, showing the fibrous fasteners for releasably securing the forward and rearward arm members for convenient storage of the gripping device of the present invention.

With reference again to FIGS. 1-7, and with further reference to FIGS. 16-18, the forwardmost portion of the channel-shaped rearward arm member 12 has a respective first pair of plates 62 and 63 secured thereto by rivets 64 (or other suitable means) and extending forwardly thereof. The rearward-most portion of the complementary channel-shaped forward arm member 11 has a respective second pair of plates 65 and 66 secured thereto by rivets 67 (or other suitable means) and extending rearwardly therefrom to partially straddle the first plates 63, and 64, respectively. These pairs of plates are connected together by a hinge pin 68 carrying cap nuts 69, thereby constituting the hinge means for pivotably mounting the forward arm member on the rearward arm member.

With this arrangement, and as shown more clearly in the sequence views of FIGS. 19-22, the forward arm member 11 may be swung back and folded over on a portion of the rearward arm member 11, respectively. The forward arm member carries a fibrous fastener 70, while the rearward arm member carries a complementary fibrous fastener 71. These fasteners releasably engage each other as shown in FIG. 22, to retain the forward arm member in its folded back position on the rearward arm member. In this folded position, the gripping device 10 of the present invention may be stored conveniently on the wheelchair of the handicapped person, as for example, in a vertical position on the wheelchair. The fibrous fasteners 70, 71 may be of the well-known "VELCRO" type; one of the fasteners constitutes the "hooks" and the other "loops".

With reference again to FIGS. 1, 16 and 18, the rearwardly-extending portions of the plates 65 and 66 carried by the forward arm member 11, which straddle the respective plates 62, 63 on the rearward arm member, carry a transverse stop pin 72 retained by cap nuts 73. The stop pin 72 limits the downward (gravity-influenced) pivotal movement of the forward arm member 11 relative to the rearward arm member 12. When the stop pin 72 engages the rearward arm member 12, as shown in FIG. 16, the forward arm member 11 and the rearward arm member 12 together have a substantially straight line configuration. With reference again to FIG. 1, the toggle control mechanism 15 is pivotably mounted, as at 74, on a bracket 75 secured on top of the rearward arm members.

Obviously, many modifications may be made without departing from the basic spirit of the present invention. Accordingly, within the scope of the appended claims, the invention may be practiced other than specifically disclosed herein.

What is claimed is:

1. A gripping device to aid handicapped persons in reaching and picking up objects, wherein the device substantially satisfies the needs of handicapped persons with minimal or no finger function, severe wrist deformities, and little or minimally functional trunk musculature, the device including a forward arm member carrying a gripping means forwardly thereon, a rearward arm member having a right side and a left side pivotally connected to the forward arm member, a control mechanism for selectively controlling the gripping means, a palm brace secured to the rearward arm member and depending therefrom and a bracing means for providing a three-point lateral restraint system, said bracing means comprising a wrist brace mounted on the rearward arm member rearwardly of the palm brace and positioned proximally to the wrist of the user when the palm brace is pressed by the palm of the user, the wrist brace being devoid of a rigid connection to the wrist of the handicapped person, whereby the wrist brace substantially immobilizes the wrist against either non-functional flexion or extension, a thumb support mounted in juxtaposition to the palm brace and having an opening adapted to receive the thumb of the user when the palm brace is pressed, wherein the sole purpose of the thumb support is to provide a vertical restraint preventing the wrist from dropping downwardly, and an arm support carried on the device rearwardly of the wrist brace.

2. The gripping device of claim 1, wherein the rearward arm member has a rear portion, wherein the arm support is mounted on the rear portion of the rearward arm member, and wherein the arm support at least partially surrounds the forearm of the user and cooperates with the wrist brace to substantially limit movement of the wrist joint of the user by providing said three-point lateral restraint.

3. The gripping device of claim 2, wherein the arm support comprises a substantially U-shaped formed wire having a pair of spaced-apart C-shaped loops and further having a pair of free ends, wherein the rearward arm member has a pair of complementary spaced apertures for removably receiving the respective ends of the wire-formed arm brace, and wherein the arm support forms an open loop at least partially surrounding the forearm of the user and is adaptable to either side of the gripping device so as to accommodate either arm of the user.

4. The gripping device of claim 1, wherein the gripping means comprises a pair of gripping tongs, and wherein the control mechanism comprises a toggle pivotably mounted on the top of the rearward arm member, a spring having a pair of ends and nested within the rearward arm member, a substantially Vee-shaped wire beneath the forward arm member and having a bight and further having a pair of free ends extending forwardly therefrom, means for connecting the free ends of the Vee-shaped wire to the gripping tongs, respectively, a first cord connecting the bight of the Vee-shaped wire to an end of the spring, and a second cord connecting the other end of the spring to the toggle.

5. The improvement of claim 4, further including a pair of prongs extending laterally of the toggle to facilitate actuation thereof.

6. In a gripping device to aid handicapped persons in reaching and picking up objects, wherein a forward arm member carries a gripping means forwardly thereon, wherein a rearward arm member having a right side and a left side is pivotally connected to the forward arm member, wherein a control mechanism is provided for selectively controlling the gripping means, and wherein a palm brace is secured to the rearward arm member and depends therefrom: the improvement of bracing means comprising a wrist brace mounted on the rearward arm member rearwardly of the palm brace and positioned proximally to the wrist of the user when the palm brace is pressed by the user, thereby limiting the non-functional flexion or extension of the wrist joint, a thumb support mounted adjacent to the palm brace and having an opening adapted to receive the thumb of the user when the palm brace is pressed, and an arm support carried on the device rearwardly of the wrist brace, wherein the wrist brace comprises an elongaged, substantially U-shaped formed wire having a pair of ends, and wherein the rearward arm member has a pair of complementary apertures accessible from each side thereof for receiving the respective ends of the formed wrist brace, whereby the wrist brace may be removably mounted on either side of the rearward arm member, thereby allowing the gripping device to be worn on either arm of the user.

7. In a gripping device to aid handicapped persons in reaching and picking up objects, wherein a forward arm member carries a gripping means forwardly thereon, wherein a rearward arm member having a right side and a left side is pivotally connected to the forward arm member, wherein a control mechanism is provided for selectively controlling the gripping means, and wherein a palm brace is secured to the rearward arm member and depends therefrom: the improvement of bracing means comprising a wrist brace mounted on the rearward arm member rearwardly of the palm brace and positioned proximally to the wrist of the user when the palm brace is pressed by the user, thereby limiting the non-functional flexion or extension of the wrist joint, a thumb support mounted adjacent to the palm brace and having an opening adapted to receive the thumb of the user when the palm brace is pressed, and an arm support carried on the device rearwardly of the wrist brace, wherein the thumb support comprises a, substantially U-shaped formed wire having a pair of ends, and wherein the palm brace and rearward member each has a respective complementary aperture accessible from each side thereof to receive the ends of the wire, whereby the thumb support may be mounted on either side of the gripping device, and whereby the thumb support forms a closed loop accommodating the thumb of either hand of the user.

8. In a gripping device to aid handicapped persons in reaching and picking up objects, wherein a forward arm member having respective right and left sides carries a gripping means forwardly thereon, wherein a rearward arm member having respective right and left sides is pivotally connected to the forward arm member, wherein a control mechanism is provided for selectively controlling the gripping means, and wherein a palm brace is secured to the rearward arm member and depends therefrom: the improvement of bracing means comprising a thumb support mounted adjacent to the palm brace and having an opening adapted to receive the thumb of the user when the palm brace is pressed, the thumb support being formed as a substantially U-shaped formed wire having a pair of ends, and wherein the palm brace and rearward arm member each has a respective complementary aperture accessible from each side thereof to receive the ends of the wire, whereby the thumb support may be mounted on either side of the gripping device, and whereby the thumb support forms a closed loop accommodating the thumb of either hand of the user, a wrist brace mounted on the rearward arm member rearwardly of the palm brace and positioned proximally to the wrist of the user when the palm brace is pressed by the user, thereby limiting the non-functional flexion or extension of the wrist joint, an arm support mounted on the rearward arm member rearwardly of the wrist brace, wherein the arm support at least partially surrounds the forearm of the user and cooperates with the wrist brace to substantially limit the movement of the wrist joint of the user by providing a three-point lateral restraint, wherein the wrist brace and arm support are removably mounted and are adaptable to either side of said rearward arm member, thereby allowing the gripping device to be worn on either arm of the user, wherein the wrist brace comprises an elongated, substantially U-shaped formed wire having a pair of ends, wherein the rearward arm member has a pair of complementary apertures accessible from each side thereof for receiving the respective ends of the wire-formed wrist brace, whereby the wrist brace may be removably mounted on either side of the rearward arm member, thereby allowing the gripping device to be worn on either arm of the user, wherein the arm support comprises a substantially U-shaped formed wire having a pair of spaced-apart C-shaped loops and further having a pair of free ends, wherein the rearward arm member has a pair of complementary spaced apertures for removably receiving the respective ends of the wire-formed arm support, and wherein the arm support forms an open loop at least partially surrounding the forearm of the user and is adaptable to either side of the gripping device.

9. The improvement of claim 8, further including a lanyard having a cord provided with a pair of ends including one end and an other end, neans for securing the one end of the lanyard cord to the control mechanism, and a self-adjusting noose formed on the other end of the lanyard cord, whereby the noose may be engaged by the user to actuate the control mechanism.

10. The improvement of claim 9, further including a ball slidably carried on the noose.

11. The improvement of claim 8, wherein each of the forward and rearward arm members are made of substantially U-shaped channels.

12. In a gripping device to aid handicapped persons in reaching and picking up objects, wherein a forward arm member carries a gripping means forwardly thereon, wherein a rearward arm member having a right side and a left side is pivotally connected to the forward arm member, wherein a control mechanism is provided for selectively controlling the gripping means, and wherein a palm brace is secured to the rearward arm member and depends therefrom: the improvement of bracing means comprising a wrist brace mounted on the rearward arm member rearwardly of the palm brace and positioned proximally to the wrist of the user when the palm brace is pressed by the user, thereby limiting the non-functional flexion or extension of the wrist joint, a thumb support mounted adjacent to the palm brace and having an opening adapted to receive the thumb of the user when the palm brace is pressed, and an arm support carried on the device rearwardly of the wrist brace, further including a hinge for pivotally connecting the forward and rearward arm members, the hinge comprising respective first plates secured to the right and left sides of the rearward arm member and having respective portions extending forwardly therefrom, respective second plates secured to the right and left sides of the forward arm member and, further including a hinge for pivotally connecting the forward and rearward arm members, the hinge comprising respective first plates secured to the right and left sides of the rearward arm member and having respective portions extending forwardly therefrom, respective second plates secured to the right and left sides of the forward arm member and having respective portions extending rearwardly therefrom and partially straddling the respective first plates secured to the rearward arm member, a transverse hinge pin connecting the respective extending portions of the respective first and second plates, whereby the forward arm member may be pivotably folded back upon the rearward arm member for storage of the gripping device, and a transverse stop pin connected between the respective straddling portions of the second plates rearwardly of the hinge pin, whereby the stop pin engages the underside of the rearward arm member to limit the downward pivotal movement of the forward arm member, and whereby when the stop pin engages the rearward arm member, the forward and rearward arm members are substantially in a straight line relative to each other, further including a pair of releasable fibrous fasteners, one on the forward arm member and the other on the rearward arm member, the releasable fibrous fasteners engaging each other to retain the forward arm member in its folded back position on the rearward arm member.

13. In a gripping device to aid handicapped persons in reaching and picking up objects, wherein a forward arm member carries a gripping means forwardly thereon, wherein a rearward arm member having a right side and a left side is pivotally connected to the forward arm member, wherein a control mechanism is provided for selectively controlling the gripping means, and wherein a palm brace is secured to the rearward arm member and depends therefrom: the improvement of bracing means comprising a wrist brace mounted on the rearward arm member rearwardly of the palm brace and positioned proximally to the wrist of the user when the palm brace is pressed by the user, thereby limiting the non-functional flexion or extension of the wrist joint, a thumb support mounted adjacent to the palm brace and having an opening adapted to receive the thumb of the user when the palm brace is pressed, and an arm support carried on the device rearwardly of the wrist brace, further including a hinge for pivotally connecting the forward and rearward arm members, the hinge comprising respective first plates secured to the right and left sides of the rearward arm member and having respective portions extending forwardly therefrom, respective second plates secured to the right and left sides of the forward arm member and having respective portions extending rearwardly therefrom and partially straddling the respective first plates secured to the rearward arm member, a transverse hinge pin connecting the respective extending portions of the respective first and second plates, whereby the forward arm member may be pivotably folded back upon the rearward arm member for storage of the gripping device, and a transverse stop pin connected between the respective straddling portions of the second plates rearwardly of the hinge pin, whereby the stop pin engages the underside of the rearward arm member to limit the downward pivotal movement of the forward arm member, and whereby when the stop pin engages the rearward arm member, the forward and rearward arm members are substantially in a straight line relative to each other, further including a pair of releasable fibrous fasteners, one on the forward arm member and the other on the rearward arm emmber, the releasable fibrous fasteners engaging each other other to retain the forward arm member in its folded back position on the rearward arm member.

14. In a gripping device to aid a handicapped person in reaching and picking up an object, wherein the device substantially satisfies the needs of handicapped persons with minimal or no finger function, severe wrist deformities, and little or minimally functional trunk musculature, the combination of a pair of gripping tongs, a resiliently-biased pivotable control including a toggle mechanism having an over-the-center spring action for selectively actuating the gripping tongs, bracing means providing a three-point lateral restraint for the wrist of the user, said bracing means including a palm brace carried by the device and depending therefrom between the gripping tongs and the toggle mechanism, a wrist brace carried by the device rearwardly of the palm brace and disposed adjacent to the wrist of the handicapped person when the palm brace is pressed by the person's palm, whereby the wrist brace substantially immobilizes the wrist against flexion or extension, an arm support carried by the device rearwardly of the wrist brace, and a thumb support adjacent to the palm brace for the sole purpose of providing a vertical restraint against downward movement of the wrist; wherein a lanyard including a cord has one end attached to the toggle mechanism, and wherein means are provided on the other end of the cord for engagement by the other hand of the user.

15. In a gripping device to aid a handicapped person in reaching and picking up an object, wherein the device substantially satisfies the needs of handicapped persons with minimal or no finger function, severe wrist deformities, and little or minimally functional trunk musculature, the combination of a pair of gripping tongs, a resiliently-biased pivotable control including a toggle mechanism having an over-the-center spring action for selectively actuating the gripping tongs, bracing means providing a three-point lateral restraint for the wrist and forearm of the user, said bracing means including a palm brace carried by the device and depending therefrom between the gripping tongs and the toggle mechanism, a wrist brace carried by the device rearwardly of the palm brace and disposed adjacent to the wrist of the handicapped person when the palm brace is pressed by the person's palm, whereby the wrist brace substantially immobilizes the wrist against flexion or extension, an arm support carried by the device rearwardly of the wrist brace, and a thumb support adjacent to the palm brace for the sole purpose of providing a vertical restraint against downward movement of the wrist; and means for removably attaching the thumb support and wrist brace to either side of the gripping device, thereby facilitating use by either a right-handed or a left-handed person.

16. In a gripping device to aid a handicapped person in reaching and picking up an object, wherein the device substantially satisfies the needs of handicapped persons with minimal or no finger function, severe wrist deformities, and little or minimally functional trunk musculature, the combination of a pair of gripping tongs, a resiliently-biased pivotable control including a toggle mechanism having an over-the-center spring action for selectively actuating the gripping tongs, bracing means providing a three-point-lateral restraint for the wrist and forearm of the user, said bracing means including a palm brace carried by the device and depending therefrom between the gripping tons and the toggle mechanism, a wrist brace carried by the device rearwardly of the palm brace and disposed adjacent to the wrist of the handicapped person when the palm brace is pressed by the person's palm, whereby the wrist brace substantially immobilizes the wrist against flexion or extension, an arm support carried by the device rearwardly of the wrist brace, and a thumb support adjacent to the palm brace for the sole purpose of providing a vertical restraint against downward movement of the wrist; the arrangement being such that the forces generated by the wrist brace on the one hand, and the arm support and palm brace on the other hand, are substantially opposed to one another; and means for removably attaching the thumb support, wrist brace and arm support to either side of the gripping device, thereby facilitating use by either a right-handed or a left-handed person.

17. In a gripping device to aid a handicapped person in reaching and picking up an object, wherein the device substantially satisfies the needs of handicapped persons with minimal or no finger function, severe wrist deformities, and little or minimally functional trunk musculature, the combination of a pair of gripping tongs, a resiliently-biased pivotable control including a toggle mechanism ahving an over-the-center spring action for selectively actuating the gripping tongs, bracing means providing a three-point lateral support for the wrist and forearm of the user, while providing a substantially straight line extension of the forearm, said bracing means including a palm brace carried by the device and depending therefrom between the gripping tongs and the toggle mechanism, a wrist brace carried by the device rearwardly of the palm brace and disposed adjacent to the wrist of the handicapped person when the palm brace is pressed by the person's palm, whereby the wrist brace substantially immobilizes the wrist against flexion or extension, an arm support carried by the device rearwardly of the wrist brace, and a thumb support adjacent to the palm brace for the sole purpose of providing a vertical restraint against downward movement of the wrist; wherein the thumb support, wrist brace and arm support are each formed from wire bent into substantially U-shaped forms, respectively.

18. A gripping device to be used on the forearm of a handicapped person on reaching and picking up an object, comprising a forward arm member, a pair of gripping tongs carried by the forward arm member and extending forwardly therefrom, a rearward arm member, means including a hinge for connecting the forward and rearward arm members and allowing the forward arm member to be folded back and over the rearward arm member, releasable means for retaining the forward arm member in its folded back position on the rearward arm member, means for limiting the downward pivotal movement of the forward arm member relative to the rearward arm member, such that the forward and rearward arm members when extended are in substantially a straight line relative to each other, a toggle control mechanism carried by the rearward arm member and having an over-the-center spring action for selectively opening and closing the gripping tongs, and bracing means providing a lateral restraint, while lining up the gripping device as a substantially straight line extension of the forearm.

19. The gripping device of claim 18, wherein the bracing means provides a three-point lateral restraint.

* * * * *